US006281347B1

(12) United States Patent
O'Donnell et al.

(10) Patent No.: US 6,281,347 B1
(45) Date of Patent: Aug. 28, 2001

(54) HUMAN ORIGIN OF REPLICATION COMPLEX GENES AND USES THEREOF

(76) Inventors: Michael O'Donnell, 16 Maple La., Hastings-on-Hudson, NY (US) 10706; Frank Dean, 253 E. 82$^{nd}$ St., Apt. B-8, New York, NY (US) 10028; Irena Bruck, 1161 York Ave., Apt. 11M, New York, NY (US) 10021

( * ) Notice: Subject to any disclaimer, the term of this patent is extended or adjusted under 35 U.S.C. 154(b) by 0 days.

(21) Appl. No.: 09/150,213

(22) Filed: Sep. 9, 1998

Related U.S. Application Data

(60) Provisional application No. 60/058,479, filed on Sep. 10, 1997.

(51) Int. Cl.[7] .................................................... C07H 21/04
(52) U.S. Cl. .................... 536/23.5; 536/23.1; 435/320.1; 435/325; 435/252.3; 435/252.33
(58) Field of Search ................................. 536/23.1, 23.5; 435/6, 320.1, 325, 252.3, 252.33

(56) References Cited

U.S. PATENT DOCUMENTS

| | | | |
|---|---|---|---|
| 5,589,341 | * 12/1996 | Stillman et al. | ............................ 435/6 |
| 5,614,618 | 3/1997 | Stillman et al. | ...................... 536/23.1 |

FOREIGN PATENT DOCUMENTS

WO 95/16694 of 0000 (EP) .

OTHER PUBLICATIONS

Quintana et al., "Identification of HsORC4, a Member of the Human Origin of Replication Recognition Complex," *The Journal of Biological Chemistry*, 272(45):28247–28251 (1997).
Ishiai et al., "Isolation of Human and Fission Yeast Homologues of the Budding Yeast Origin Recognition Complex Subunit ORC5: Human Homologue (ORC5L) Maps to 7q22," *Genomics*, 46:294–298 (1997).
Bell et al., "ATP–dependent Recognition of Eukaryotic Origins of DNA Replication by a Multiprotein Complex," *Nature*, 357:128–134 (1992).
Muzi–Falconi et al., "Orp1, A Member of the Cdc18/Cdc6 Family of S–phase Regulators, is Homologous to a Component of the Origin Recognition Complex," *Proc. Natl. Acad. Sci. USA*, 92:12475–12479 (1995).

Gavin et al., "Conserved Initiator proteins in Eukaryotes," *Science*, 270:1667–71 (1995).
Donovan et al., "Replication Origins of Eukaryotes," *Curr. Opin. Genet. Dev.*, 6(2):203–7 (1996) (abstract).
Loo et al., "Silencing and Heritable Domains of Gene Expression," *Ann. Rev. Cell. Dev. Biol.*, 11:519–48 (1995) (abstract).
Hardy, "Characterization of an Essential Orc2p–Associated Factor That Plays a Role in DNA Replication," *Mol. Cell Biol.*, 16(4):1832–41 (1996).
Bell et al., "The Multidomain Structure Orc1p Reveals Similarity to Regulators of DNA Replication and Transcriptional Silencing," *Cell*, 83:563–568 (1995).
Loo et al., "The Origina Recognition Complex in Silencing, Cell Cycle Progression, and DNA Replication," *Mol. Biol. Cell*, 6:741–756 (1995).
Fox et al., "The Origin Recognition Complex has Essential Functions in Transcriptional Silencing and Chromosomal Replication," *Genes Dev.*, 9:911–924 (1995).
Liang et al., "ORC and Cdc6p Interact and Determine the Frequency of Initiation of DNA Replication in the Genome," *Cell*, 81:667–676 (1995).
Kelly et al., "Replication and Transcription. Silence of the ORCs," *Curr. Biol.*, 4(3):238–41 (1994).
Marahrens et al., "Replicator Dominance in a Eukaryotic Chromosome," *EMBO J.*, 13(14):3395–3400 (1994).
Takahara et al., "Mouse and Human Homologues of the Yeast Origin of Replication Recognition Complex Subunit ORC2 and Chromosomal Localization of the Cognate Human Gene ORC2L," *Genomics*, 31(1):119–22 (1996) (abstract).

\* cited by examiner

*Primary Examiner*—Remy Yucel
(74) *Attorney, Agent, or Firm*—Nixon Peabody LLP

(57) ABSTRACT

The present invention relates to an isolated DNA molecule encoding human origin of recognition complex subunit 4 protein or polypeptide or human origin of recognition complex subunit 5 protein or polypeptide. Also disclosed is the isolated human origin of recognition complex subunit 4 protein or polypeptide or human origin of recognition complex subunit 5 protein or polypeptide. These materials can be used in identifying lead compounds for a pharmacological agent which are useful in diagnosing and treating disease associated with cell growth.

23 Claims, 4 Drawing Sheets

HUMAN ORIGIN OF REPLICATION COMPLEX GENES AND USES THEREOF

This application is entitled to benefit of U.S. Provisional Patent Application Ser. No. 60/058,479, filed Sep. 10, 1997.

The present invention was developed under National Institutes of Health, Grant No. GM 38837. The U.S. Government may have certain rights.

FIELD OF THE INVENTION

The present invention is directed to human origin of replication complex genes and their uses.

BACKGROUND OF THE INVENTION

DNA replication in eukaryotic cells is tightly controlled and coordinated with other events during the cell cycle and cell proliferation. Studies carried out with the budding yeast, *Saccharomyces cerevisiae*, led to the identification of an origin recognition complex ("ORC") (Bell, S. P., et al., "ATP-dependent Recognition of Eukaryotic Origins of DNA Replication by a Multiprotein Complex,"*Nature,* 357:128–34 (1992)). ORC consists of six polypeptides (i.e. ORC1 to ORC6) and plays an essential role in the initiation of chromosome DNA replication and transcriptional silencing in the budding yeast (Bell, S. P., et al., "Yeast Origin Recognition Complex Functions in Transcription Silencing and DNA Replication," *Science,* 262:1844–49 (1993); Bell, S. P., et al., "ATP-dependent Recognition of Eukaryotic Origins of DNA Replication by a Multiprotein Complex," *Nature,* 357:128–34 (1992); Micklem, G., et al., "Yeast Origin Recognition Complex is Involved in DNA Replication and Transcriptional Silencing," *Nature,* 366:87–89 (1993)). This six-protein complex binds to several well defined autonomously replicating sequences that serve as the chromosomal replication origins in an ATP-dependent manner (Bell, S. P., et al., "ATP-dependent Recognition of Eukaryotic Origins of DNA Replication by a Multiprotein Complex," *Nature,* 357:128–34 (1992)). The genes for all six ORC subunits have been isolated and deletion of any one of these genes results in lethality (Bell, S. P., et al., "Yeast Origin Recognition Complex Functions in Transcription Silencing and DNA Replication," *Science,* 262:1844–49 (1993); Bell, S. P., et al., "The Multidomain Structure of Orc 1 p Reveals Similarity to Regulators of DNA Replication and Transcriptional Silencing," *Cell,* 83:563–68 (1995); Foss, et al., "Origin Recognition Complex (ORC) in Transcriptional Silencing and DNA Replication in *S. cerevisiae,*" *Science,* 262:1838–44 (1993); Li, J. J., et al., "Isolation of ORC6, a Component of the Yeast Origin Recognition Complex by a One-Hybrid System," *Science,* 262:1870–74 (1993); Loo, S., et al., "The Origin Recognition Complex in Silencing, Cell Cycle Progression, and DNA Replication," *Mol. Biol. Cell,* 6:741–56 (1995); Micklem, G., et al., "Yeast Origin Recognition Complex is Involved in DNA Replication and Transcriptional Silencing," *Nature,* 366:87–89 (1993)). The regulation of initiation of metazoan chromosomal DNA replication is poorly understood, because chromosomal origins have not been localized to specific DNA sequences. Recently, cDNA clones encoding proteins homologous to the *S. cerevisiae* ORC have been isolated from *Schizosaccharomyces pombe*, *Xenopus laevis*, and human for both ORC1 and ORC2, from *kluyveromyces lactis* for ORC1, and from *Caenorhabditis elegans*, *Arabidopsis thaliana* and mouse for ORC2 (Carpenter, P. B., et al., "Role for a Xenopus Orc2-related Protein in Controlling DNA Replication," *Nature,* 379:357–60 (1996); Gavin, K. A., et al., "Conserved Initiator Proteins in Eukaryotes," *Science,* 270:1667–71 (1995); Leatherwood, J., et al., "Interaction of Cdc2 and Cdc18 with a Fission Yeast ORC2-like Protein," *Nature,* 379:360–63 (1996); Muzi-Falconi, M., et al., "Orp1, a Member of the Cdc18/Cdc6 Family of S-phase Regulators, is Homologous to a Component of the Origin Recognition Complex," *Proc. Natl. Acad. Sci. USA,* 92:12475–79 (1995); Rowles, A., et al., "Interaction Between the Origin Recognition Complex and the Replication Licensing System in Xenopus," *Cell,* 87:287–96 (1996); Takahara, K., et al., "Mouse and Human Homologues of the Yeast Origin of Replication Recognition Complex Subunit ORC2 and Chromosomal Localization of the Cognate Human Gene ORC2L," *Genomics,* 31:119–22 (1996)). The Orc2 and Orc5 homologues have also been cloned from *Drosophila melanogaster* (Gossen, M., et al., "A Drosophila Homolog of the Yeast Origin Recognition Complex," *Science,* 270:1674–77 (1995)). A multisubunit protein complex made up of subunits homologous to the *S. cerevisiae* ORC genes has been purified from Drosophila and Xenopus (Gossen, M., et al., "A Drosophila Homolog of the Yeast Origin Recognition Complex," *Science,* 270:1674–77 (1995); Rowles, A., et al., "Interaction Between the Origin Recognition Complex and the Replication Licensing System in Xenopus," *Cell,* 87:287–96 (1996)).

Although origin of recognition complex subunits have been isolated and sequenced in some species, including human (i.e. ORC1 and ORC2), the need remains for such work to be carried out for other subunits. The present invention is directed to fulfilling this objective.

SUMMARY OF THE INVENTION

The present invention relates to isolated DNA molecules encoding human origin of recognition complex subunit 4 and human origin of recognition complex subunit 5. Also disclosed is the isolated human origin of recognition complex subunit 4 protein or polypeptide and the human origin of recognition complex subunit 5 protein or polypeptide.

Another aspect of the present invention relates to a method of identifying compounds for a pharmacological agent useful in the diagnosis or treatment of disease associated with cell growth. This method involves forming a mixture comprising (1) either a human origin of recognition complex subunit 4 protein or polypeptide or a human origin of recognition complex subunit 5 protein or polypeptide, (2) an intracellular protein binding target capable of specifically binding to human origin of recognition complex 4 protein or polypeptide or a human origin of recognition complex subunit 5 protein or polypeptide, and (3) a candidate pharmacological agent. The mixture is then incubated under conditions effective, but for the candidate pharmacological agent, for the human origin of recognition complex subunit 4 protein or polypeptide or the human origin of recognition complex subunit 5 protein or polypeptide to bind to the binding target. The presence or absence of specific binding of the human origin of recognition complex subunit 4 protein or polypeptide or the human origin of recognition complex subunit 5 protein or polypeptide to the binding target is then detected. The absence of selective binding indicates that the candidate pharmacological agent is a lead compound that disrupts cellular function of the human origin of recognition complex subunit 4 protein or polypeptide or the human origin of recognition complex subunit 5 protein or polypeptide and inhibits cell growth.

BRIEF DESCRIPTION OF THE DRAWINGS

FIG. 1 shows a multiple alignment of the ORC5 homologues, Human, human being; Drome, *Drosophila*

*melanogaster* (Gossen, M., et al., "A Drosophila Homolog of the Yeast Origin Recognition Complex," *Science*, 270:1674–77 (1995), which is hereby incorporated by reference); Caeel, *Caenorhabditis elegans* ZC168.3 (Genbank Accession Number: Z70312); Yeast, *Saccharomyces cerevisiae* (Loo, S., et al., "The Origin Recognition Complex in Silencing, Cell Cycle Progression, and DNA Replication," *Mol. Biol. Cell,* 6:741–56 (1995), which is hereby incorporated by reference) were aligned by the Clustal Method using the Megalign program (DNASTAR Inc., Wisconsin). Identical amino acids are indicated by the boxed regions.

Figure 2:
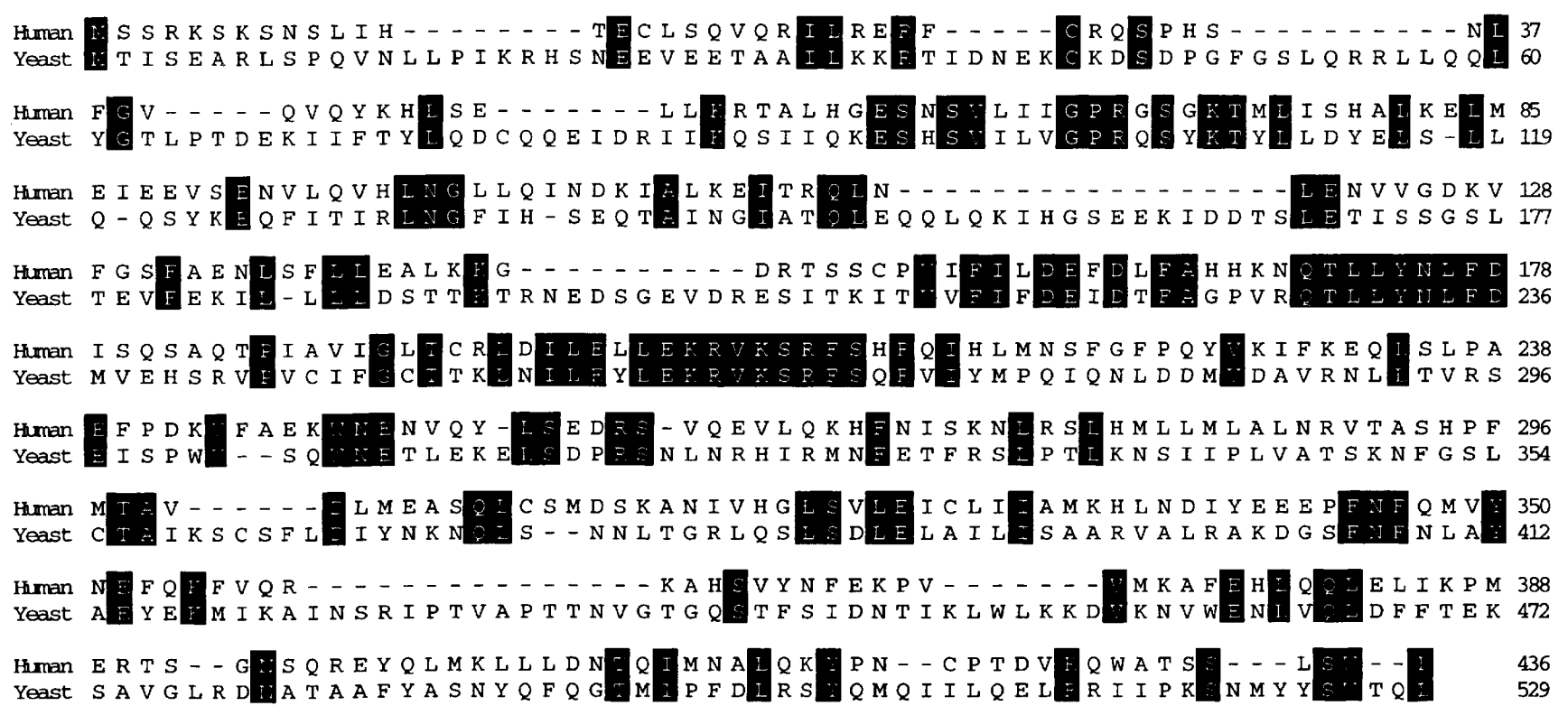

FIG. 2 shows a comparison of the ORC4 genes of human and yeast. The amino acid sequences were aligned by the Clustal method using the Megalign program (DNASTAR Inc., Wisconsin). Identical amino acids are indicated by the boxed regions.

Figure 3:
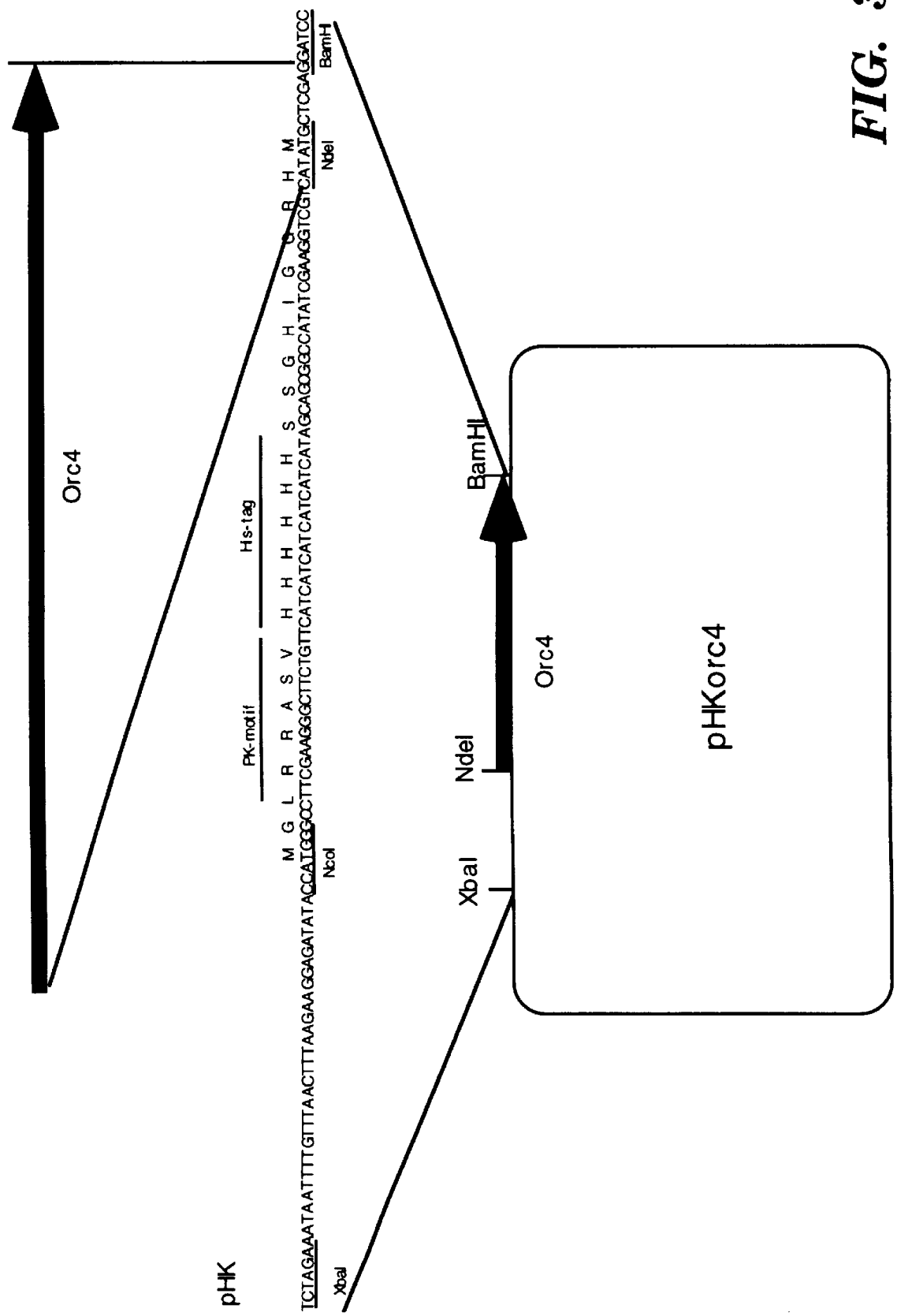

FIG. 3 shows an ORC4 expression vector. pHK vector is a modified version of a pET-16b vector (Novagen). It carries a cAMP-dependent protein kinase site, six Histidine tag, and Factor Xa site cloned into XbaI and BamHI sites of a pET-16b vector. The ORC4 gene is inserted between the NdeI and BamHI sites such that the initiating Met of ORC4 is encoded within the NdeI site. Insertion of the ORC4 gene into a pHK vector resulted in removal of the intervening nucleotides (between NdeI and BamHI).

Figure 4A:
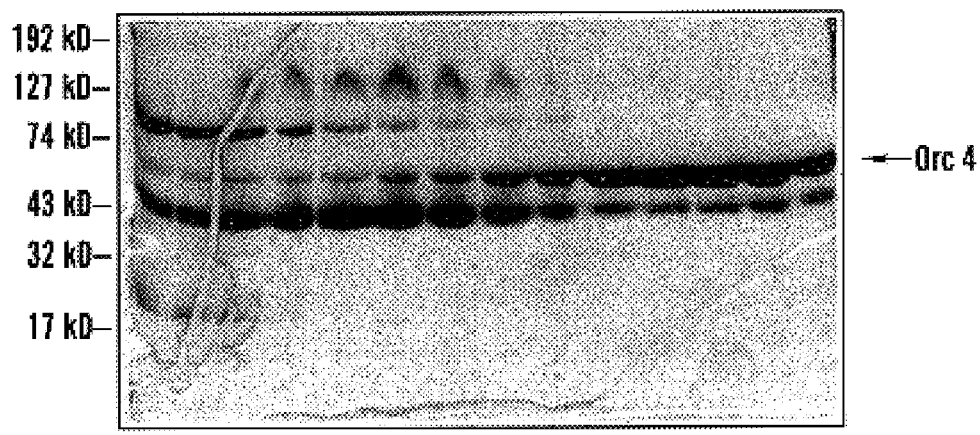
Figure 4B:
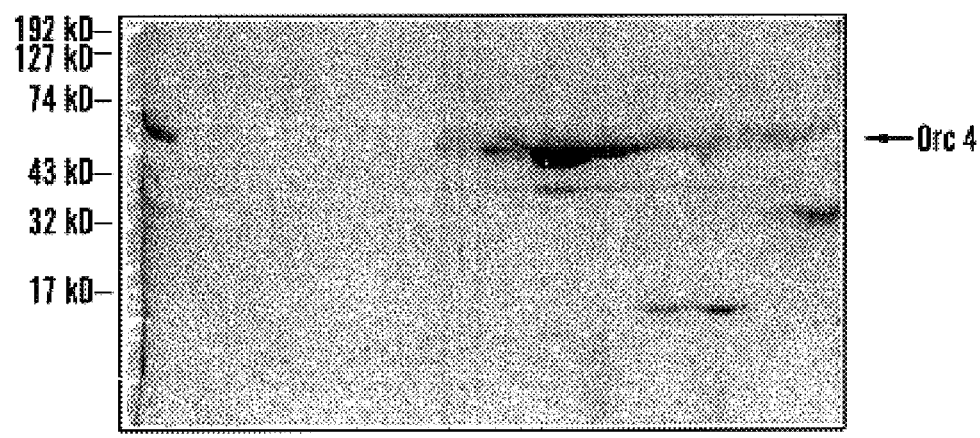

FIGS. 4A and B show the purification profile of ORC4. Proteins were separated on a 10% SDS-Polyacrylamide gel and stained with Coomassie Blue R-250. Each lane contains 20 µl from each fraction shown on the gel. The last lane contains molecular weight markers (Kaleidascope, Biorad). FIG. 4A shows an elution profile of ORC4 from an H, Trap (Pharmacia) metal chelate column. ORC4 elution starts at 170 mM imidazole. The molecular weight of ORC4 is about 50 kD. FIG. 4B shows an elution profile of ORC4 from a MonoQ column. ORC4 elutes at approximately 150 mM NaCl.

DETAILED DESCRIPTION OF THE INVENTION

The present invention relates to an isolated human origin of recognition complex subunit 4 protein or polypeptide and the DNA molecule encoding it. The isolated DNA molecule has a nucleotide sequence of SEQ. ID. No. 1 as follows:

```
ATGCCCCACT TGGAAAACGT GGTGCTTTGT CGCGAGTCTC AAGTGTCCAT CTTGCAGTCC   60
TTGTTTGGAG AGAGACATCA TTTCAGCTTT CCATCCATTT TTATTTATAG ACATACTGCT  120
AGTGGAAAGA CCTATGTAAC ACAAACGTTG TTGAAAACTT TAGAGCTCCC ACATGTGTTT  180
GTGAATTGTG TTGAATGCTT TACATTGAGG CTGCTTTTGG AACAAATTTT AAACAAATTG  240
AATCATCTTA GTTCTTCAGA GGATGGATGT TCTACTGAAA TAACCTGTGA AACATTTAAT  300
GACTTTGTTC GCTTGTTTAA ACAAGTAACC ACAGCTGAAA ATCTTAAAGA TCAGACTGTA  360
TATATTGTTC TAGATAAAGC AGAGTATCTA AGAGATATGG AAGCAAATCT TTTGCCTGGA  420
TTTCTTAGAT TACAAGAATT GGCTGACAGA AATGTGACTG TTCTCTTTCT CAGTGAAATT  480
GTTTGGGAAA AGTTTCGTCC AAATACTGGA TGCTTTGAGC CGTTTGTCTT ATATTTCCCT  540
GATTACAGCA TAGGCAACCT TCAAAAGATC CTGTCCCATG ATCATCCTCC AGAGTATTCA  600
GCTGATTTCT ATGCTGCCTA CATTAACATT CTTCTTGGAG TTTTCTACAC TGTTTGTCGA  660
GATTTGAAAG AGCTCAGACA TCTGGCAGTA CTTAATTTTC CTAAATATTG TGAACCCGTG  720
GTTAAAGGAG AAGCAAGTGA ACGTGATACT CGCAAACTGT GGAGAAATAT TGAACCTCAT  780
TTGAAGAAAG CTATGCAGAC TGTTTATCTC AGGGAAATAT CAAGTTCCCA GTGGGAAAAG  840
CTACAGAAAG ATGACACAGA TCCGGGGCAA CTGAAAGGCC TCTCAGCGCA TACTCATGTG  900
GAACTTCCAT ATTACTCTAA GTTCATTCTA ATTGCTGCAT ACCTTGCTTC ATACAATCCA  960
GCAAGAACTG ACAAGAGGTT TTTTCTTAAG CATCATGGAA AAATCAAGAA AACCAACTTT 1020
CTAAAAAAAC ACGAAAAGAC AAGCAATCAT CTCCTTGGGC CAAAACCATT TCCACTAGAC 1080
AGATTATTAG CAATATTATA TAGTATCGTG GACAGCAGAG TTGCTCCAAC AGCAAATATT 1140
TTTTCCCAGA TTACCTCTCT AGTGACCCTT CAGCTGTTAA CCCTGGTTGG CCATGACGAT 1200
CAGCTTGATG GACCAAAATA CAAATGCACA GTGTCTCTAG ACTTCATCAG AGCTATTGCA 1260
AGGACGGTGA ACTTTGACAT AATAAAATAC TTGTATGATT TCTTGTGA              1308
```

The isolated human origin of recognition complex subunit 4 protein or polypeptide has an amino acid sequence of SEQ. ID. No. 2 as follows:

```
Met Pro His Leu Glu Asn Val Val Leu Cys Arg Glu Ser Gln Val Ser
1               5                   10                  15
Ile Leu Gln Ser Leu Phe Gly Glu Arg His His Phe Ser Phe Pro Ser
            20                  25                  30
Ile Phe Ile Tyr Arg His Thr Ala Ser Gly Lys Thr Tyr Val Thr Gln
                35                  40                  45
Thr Leu Leu Lys Thr Leu Glu Leu Pro His Val Phe Val Asn Cys Val
50                  55                  60
Glu Cys Phe Thr Leu Arg Leu Leu Leu Glu Gln Ile Leu Asn Lys Leu
65                      70                  75                  80
Asn His Leu Ser Ser Ser Clu Asp Gly Cys Ser Thr Glu Ile Thr Cys
                85                  90                  95
Glu Thr Phe Asn Asp Phe Val Arg Leu Phe Lys Gln Val Thr Thr Ala
                100                 105                 110
Glu Asn Leu Lys Asp Gln Thr Val Tyr Ile Val Leu Asp Lys Ala Glu
            115                 120                 125
Tyr Leu Arg Asp Met Glu Ala Asn Leu Leu Pro Gly Phe Leu Arg Leu
            130                 135                 140
Gln Glu Leu Ala Asp Arg Asn Val Thr Val Leu Phe Leu Ser Glu Ile
145                 150                 155                 160
Val Trp Glu Lys Phe Arg Pro Asn Thr Gly Cys Phe Glu Pro Phe Val
                165                 170                 175
Leu Tyr Phe Pro Asp Tyr Ser Ile Gly Asn Leu Gln Lys Ile Leu Ser
                180                 185                 190
His Asp His Pro Pro Glu Tyr Ser Ala Asp Phe Tyr Ala Ala Tyr Ile
            195                 200                 205
Asn Ile Leu Leu Gly Val Phe Tyr Thr Val Cys Arg Asp Leu Lys Glu
    210                 215                 220
Leu Arg His Leu Ala Val Leu Asn Phe Pro Lys Tyr Cys Glu Pro Val
225                 230                 235                 240
Val Lys Gly Glu Ala Ser Glu Arg Asp Thr Arg Lys Leu Trp Arg Asn
                245                 250                 255
Ile Glu Pro His Leu Lys Lys Ala Met Gln Thr Val Tyr Leu Arg Glu
            260                 265                 270
Ile Ser Ser Ser Gln Trp Glu Lys Leu Gln Lys Asp Asp Thr Asp Pro
        275                 280                 285
Gly Gln Leu Lys Gly Leu Ser Ala His Thr His Val Glu Leu Pro Tyr
    290                 295                 300
Tyr Ser Lys Phe Ile Leu Ile Ala Ala Tyr Leu Ala Ser Tyr Asn Pro
305                 310                 315                 320
Ala Arg Thr Asp Lys Arg Phe Phe Leu Lys His His Gly Lys Ile Lys
                325                 330                 335
Lys Thr Asn Phe Leu Lys Lys His Glu Lys Thr Ser Asn His Leu Leu
            340                 345                 350
Gly Pro Lys Pro Phe Pro Leu Asp Arg Leu Leu Ala Ile Leu Tyr Ser
            355                 360                 365
Ile Val Asp Ser Arg Val Ala Pro Thr Ala Asn Ile Phe Ser Gln Ile
    370                 375                 380
Thr Ser Leu Val Thr Leu Gln Leu Leu Thr Leu Val Gly His Asp Asp
385                 390                 395                 400
Gln Leu Asp Gly Pro Lys Tyr Lys Cys Thr Val Ser Leu Asp Phe Ile
                405                 410                 415
Arg Ala Ile Ala Arg Thr Val Asn Phe Asp Ile Ile Lys Tyr Leu Tyr
            420                 425                 430
Asp Phe Leu
        435
```

This protein or polypeptide has a molecular weight of 50 to 51, preferably 50.3 kDa.

The present invention also relates to an isolated human origin of recognition complex subunit 5 protein or polypeptide and the DNA molecule encoding it. The isolated DNA molecule has a nucleotide sequence of SEQ. ID. No. 3 as follows:

```
ATGAGCAGTC GTAAATCAAA GAGTAACAGC TTAATTCACA CAGAGTGCCT TTCACAGGTA    60

CAAAGAATTT TACGTGAAAG ATTTTGTCGT CAGAGTCCAC ATAGTAACCT ATTTGGAGTG   120

CAAGTACAAT ACAAACACTT AAGTGAGCTG CTGAAAAGAA CTGCTCTCCA TGGAGAGAGT   180

AACTCTGTCC TTATTATCGG ACCCCGAGGA TCAGGAAAAA CTATGTTAAT AAGTCATGCT   240

TTGAAAGAAC TCATGGAAAT AGAAGAAGTG AGTGAAAATG TATTACAAGT TCACTTAAAT   300

GGACTGCTGC AGATCAATGA CAAAATCGCC CTAAAGGAAA TCACAAGGCA GTTAAATCTG   360

GAAAATGTAG TTGGAGATAA AGTTTTTGGA AGCTTTGCTG AAAACCTTTC ATTTCTTCTG   420
```

-continued

```
GAAGCTTTAA AAAAAGGTGA CCGAACTAGC AGTTGCCCAG TGATCTTCAT ATTAGATGAA   480

TTTGATCTTT TTGCTCATCA TAAAAACCAA ACACTTCTCT ATAATCTTTT TGACATTTCT   540

CAGTCTGCAC AGACCCCAAT AGCAGTTATT GGTCTTACAT GTAGATTGGA TATTTTGGAA   600

CTCTTAGAAA AAAGAGTGAA GTCAAGATTT TCTCACCGGC AGATACACTT AATGAATTCA   660

TTTGGTTTTC CACAGTATGT TAAAATATTT AAAGAACAGT TATCTCTACC TGCAGAGTTT   720

CCAGACAAGG TTTTTGCTGA GAAGTGGAAT GAAAATGTTC AGTATCTCTC AGAAGATAGA   780

AGTGTGCAAG AAGTACTACA GAAGCATTTC AATATCAGCA AAAACCTGCG GTCATTACAC   840

ATGCTATTGA TGCTTGCTTT AAATCGAGTA ACAGCATCGC ACCCATTTAT GACTGCCGTA   900

GATCTAATGG AAGCAAGCCA ACTGTGTAGC ATGGACTCGA AAGCAAATAT TGTACATGGT   960

CTATCAGTCT TGGAAATCTG TCTTATAATA GCAATGAAAC ATTTAAATGA CATCTATGAG  1020

GAAGAGCCAT TTAATTTTCA AATGGTCTAT AATGAGTTTC AGAAGTTTGT TCAAAGGAAA  1080

GCACATTCCG TTTATAATTT TGAAAAACCT GTTGTCATGA AGGCTTTTGA ACACTTGCAG  1140

CAATTAGAAT TAATAAAGCC CATGGAAAGA ACTTCAGGAA ATTCACAGAG AGAGTACCAG  1200

CTGATGAAAC TGCTTTTGGA TAATACTCAA ATTATGAATG CTCTGCAGAA ATATCCCAAC  1260

TGTCCTACAG ATGTGAGGCA GTGGGCAACA TCCTCACTAA GCTGGTTATG A           1311
```

The isolated human origin of recognition complex subunit 5 protein or polypeptide has an amino acid sequence of SEQ. ID. No. 4 as follows:

```
Met Ser Ser Arg Lys Ser Lys Ser Asn Ser Leu Ile His Thr Glu Cys
1               5                   10                  15
Leu Ser Gln Val Gln Arg Ile Leu Arg Glu Arg Phe Cys Arg Gln Ser
                20                  25                  30
Pro His Ser Asn Leu Phe Gly Val Gln Val Gln Tyr Lys His Leu Ser
            35                  40                  45
Glu Leu Leu Lys Arg Thr Ala Leu His Gly Glu Ser Asn Ser Val Leu
        50                  55                  60
Ile Ile Gly Pro Arg Gly Ser Gly Lys Thr Met Leu Ile Ser His Ala
65                  70                  75                  80
Leu Lys Glu Leu Met Glu Ile Glu Val Ser Glu Asn Val Leu Gln
                85                  90                  95
Val His Leu Asn Gly Leu Leu Gln Ile Asn Asp Lys Ile Ala Leu Lys
            100                 105                 110
Glu Ile Thr Arg Gln Leu Asn Leu Glu Asn Val Val Gly Asp Lys Val
        115                 120                 125
Phe Gly Ser Phe Ala Glu Asn Leu Ser Phe Leu Leu Glu Ala Leu Lys
    130                 135                 140
Lys Gly Asp Arg Thr Ser Ser Cys Pro Val Ile Phe Ile Leu Asp Glu
145                 150                 155                 160
Phe Asp Leu Phe Ala His His Lys Asn Gln Thr Leu Leu Tyr Asn Leu
                165                 170                 175
Phe Asp Ile Ser Gln Ser Ala Gln Thr Pro Ile Ala Val Ile Gly Leu
            180                 185                 190
Thr Cys Arg Leu Asp Ile Leu Glu Leu Leu Glu Lys Arg Val Lys Ser
        195                 200                 205
Arg Phe Ser His Arg Gln Ile His Leu Met Asn Ser Phe Gly Phe Pro
    210                 215                 220
Gln Tyr Val Lys Ile Phe Lys Glu Gln Leu Ser Leu Pro Ala Glu Phe
225                 230                 235                 240
Pro Asp Lys Val Phe Ala Glu Lys Trp Asn Glu Asn Val Gln Tyr Leu
                245                 250                 255
Ser Glu Asp Arg Ser Val Gln Glu Val Leu Gln Lys His Phe Asn Ile
            260                 265                 270
Ser Lys Asn Leu Arg Ser Leu His Met Leu Leu Met Leu Ala Leu Asn
        275                 280                 285
Arg Val Thr Ala Ser His Pro Phe Met Thr Ala Val Asp Leu Met Glu
    290                 295                 300
Ala Ser Gln Leu Cys Ser Met Asp Ser Lys Ala Asn Ile Val His Gly
305                 310                 315                 320
Leu Ser Val Leu Glu Ile Cys Leu Ile Ile Ala Met Lys His Leu Asn
                325                 330                 335
```

```
                             -continued
Asp Ile Tyr Glu Glu Glu Pro Phe Asn Phe Gln Met Val Tyr Asn Glu
            340             345             350
Phe Gln Lys Phe Val Gln Arg Lys Ala His Ser Val Tyr Asn Phe Glu
        355             360             365
Lys Pro Val Val Met Lys Ala Phe Glu His Leu Gln Gln Leu Glu Leu
    370             375             380
Ile Lys Pro Met Glu Arg Thr Ser Gly Asn Ser Gln Arg Glu Tyr Gln
385             390             395             400
Leu Met Lys Leu Leu Leu Asp Asn Thr Gln Ile Met Asn Ala Leu Gln
            405             410             415
Lys Tyr Pro Asn Cys Pro Thr Asp Val Arg Gln Trp Ala Thr Ser Ser
            420             425             430
Leu Ser Trp Leu
        435
```

This protein or polypeptide has a molecular weight of 50 to 51, preferably 50.4 kDa.

Fragments of the above polypeptide or protein are encompassed by the present invention.

Suitable fragments can be produced by several means. In the first, subclones of the gene encoding the protein of the present invention are produced by conventional molecular genetic manipulation by subcloning gene fragments. The subclones then are expressed in vitro or in vivo in bacterial cells to yield a smaller protein or peptide that can be tested for human origin of recognition complex activity according to the procedure described below.

As an alternative, fragments of human origin of recognition complex protein can be produced by digestion of a full-length human origin of recognition complex subunit protein with proteolytic enzymes like chymotrypsin or Staphylococcus proteinase A, or trypsin. Different proteolytic enzymes are likely to cleave human origin of recognition complex subunit proteins at different sites based on the amino acid sequence of the human origin of recognition complex protein. Some of the fragments that result from proteolysis may be active human origin of recognition complex.

In another approach, based on knowledge of the primary structure of the protein, fragments of the human origin of recognition complex protein gene may be synthesized by using the PCR technique together with specific sets of primers chosen to represent particular portions of the protein. These then would be cloned into an appropriate vector for increased expression of a truncated peptide or protein.

Chemical synthesis can also be used to make suitable fragments. Such a synthesis is carried out using known amino acid sequences for the human origin of recognition complex subunit protein being produced. Alternatively, subjecting a full length human origin of recognition complex to high temperatures and pressures will produce fragments. These fragments can then be separated by conventional procedures (e.g., chromatography, SDS-PAGE).

Variants may also (or alternatively) be modified by, for example, the deletion or addition of amino acids that have minimal influence on the properties, secondary structure and hydropathic nature of the polypeptide. For example, a polypeptide may be conjugated to a signal (or leader) sequence at the N-terminal end of the protein which co-translationally or post-translationally directs transfer of the protein. The polypeptide may also be conjugated to a linker or other sequence for ease of synthesis, purification, or identification of the polypeptide.

Suitable DNA molecules are those that hybridize to a DNA molecule comprising a nucleotide sequence of 50 continuous bases of SEQ. ID. Nos. 1 or 3 under stringent conditions characterized by a hybridization buffer comprising 0.9M sodium citrate ("SSC") buffer at a temperature of 37° C. and remaining bound when subject to washing with the SSC buffer at 37° C.; and preferably in a hybridization buffer comprising 20% formamide in 0.9M saline/0.09M SSC buffer at a temperature of 42° C. and remaining bound when subject to washing at 42° C. with 0.2× SSC buffer at 42° C.

The protein or polypeptide of the present invention is preferably produced in purified form (preferably at least about 80%, more preferably 90%, pure) by conventional techniques. Typically, the protein or polypeptide of the present invention is secreted into the growth medium of recombinant host cells. Alternatively, the protein or polypeptide of the present invention is produced but not secreted into growth medium. In such cases, to isolate the protein, the host cell (e.g., *E. coli*) carrying a recombinant plasmid is propagated, lysed by sonication, heat, or chemical treatment, and the homogenate is centrifuged to remove bacterial debris. The supernatant is then subjected to sequential ammonium sulfate precipitation. The fraction containing the polypeptide or protein of the present invention is subjected to gel filtration in an appropriately sized dextran or polyacrylamide column to separate the proteins. If necessary, the protein fraction may be further purified by HPLC.

The DNA molecule encoding the human origin of recognition complex polypeptide or protein can be incorporated in cells using conventional recombinant DNA technology. Generally, this involves inserting the DNA molecule into an expression system to which the DNA molecule is heterologous (i.e. not normally present). The heterologous DNA molecule is inserted into the expression system or vector in proper sense orientation and correct reading frame. The vector contains the necessary elements for the transcription and translation of the inserted protein-coding sequences.

U.S. Pat. No. 4,237,224 to Cohen and Boyer, which is hereby incorporated by reference, describes the production of expression systems in the form of recombinant plasmids using restriction enzyme cleavage and ligation with DNA ligase. These recombinant plasmids are then introduced by means of transformation and replicated in unicellular cultures including procaryotic organisms and eucaryotic cells grown in tissue culture.

Recombinant genes may also be introduced into viruses, such as vaccina virus. Recombinant viruses can be generated by transfection of plasmids into cells infected with virus.

Suitable vectors include, but are not limited to, the following viral vectors such as lambda vector system gt11, gt WES.tB, Charon 4, and plasmid vectors such as pBR322, pBR325, pACYC177, pACYC1084, pUC8, pUC9, pUC18, pUC19, pLG339, pR290, pKC37, pKC101, SV 40, pBluescript II SK +/− or KS +/− (see "Stratagene Cloning Systems" Catalog (1993) from Stratagene, La Jolla, Calif., which is hereby incorporated by reference), pQE, pIH821, pGEX, pET series (see F. W. Studier et. al., "Use of T7 RNA Polymerase to Direct Expression of Cloned Genes," *Gene Expression Technology* vol. 185 (1990), which is hereby incorporated by reference), and any derivatives thereof. Recombinant molecules can be introduced into cells via transformation, particularly transduction, conjugation, mobilization, or electroporation. The DNA sequences are cloned into the vector using standard cloning procedures in the art, as described by Sambrook et al., *Molecular Cloning: A Laboratory Manual*, Cold Springs Laboratory, Cold Springs Harbor, N.Y. (1989), which is hereby incorporated by reference.

A variety of host-vector systems may be utilized to express the protein-encoding sequence(s). Primarily, the vector system must be compatible with the host cell used. Host-vector systems include but are not limited to the following: bacteria transformed with bacteriophage DNA, plasmid DNA, or cosmid DNA; microorganisms such as yeast containing yeast vectors; mammalian cell systems infected with virus (e.g., vaccinia virus, adenovirus, etc.); insect cell systems infected with virus (e.g., baculovirus); and plant cells infected by bacteria. The expression elements of these vectors vary in their strength and specificities. Depending upon the host-vector system utilized, any one of a number of suitable transcription and translation elements can be used.

Different genetic signals and processing events control many levels of gene expression (e.g., DNA transcription and messenger RNA (mRNA) translation).

Transcription of DNA is dependent upon the presence of a promotor which is a DNA sequence that directs the binding of RNA polymerase and thereby promotes mRNA synthesis. The DNA sequences of eucaryotic promotors differ from those of procaryotic promotors. Furthermore, eucaryotic promoters and accompanying genetic signals may not be recognized in or may not function in a procaryotic system, and, further, procaryotic promotors are not recognized and do not function in eucaryotic cells.

Similarly, translation of mRNA in procaryotes depends upon the presence of the proper procaryotic signals which differ from those of eucaryotes. Efficient translation of mRNA in procaryotes requires a ribosome binding site called the Shine-Dalgarno ("SD") sequence on the mRNA. This sequence is a short nucleotide sequence of mRNA that is located before the start codon, usually AUG, which encodes the amino-terminal methionine of the protein. The SD sequences are complementary to the 3'-end of the 16S rRNA (ribosomal RNA) and probably promote binding of mRNA to ribosomes by duplexing with the rRNA to allow correct positioning of the ribosome. For a review on maximizing gene expression, see Roberts and Lauer, *Methods in Enzymology*, 68:473 (1979), which is hereby incorporated by reference.

Promotors vary in their "strength" (i.e. their ability to promote transcription). For the purposes of expressing a cloned gene, it is desirable to use strong promoters in order to obtain a high level of transcription and, hence, expression of the gene. Depending upon the host cell system utilized, any one of a number of suitable promoters may be used. For instance, when cloning in *E. coli*, its bacteriophages, or plasmids, promoters such as the T7 phage promoter, lac promotor, trp promotor, recA promotor, ribosomal RNA promotor, the $P_R$ and $P_L$ promotors of coliphage lambda and others, including but not limited, to lacUV5, ompF, bla, lpp, and the like, may be used to direct high levels of transcription of adjacent DNA segments. Additionally, a hybrid trp-lacUV5 (tac) promotor or other *E. coli* promoters produced by recombinant DNA or other synthetic DNA techniques may be used to provide for transcription of the inserted gene.

Bacterial host cell strains and expression vectors may be chosen which inhibit the action of the promotor unless specifically induced. In certain operations, the addition of specific inducers is necessary for efficient transcription of the inserted DNA. For example, the lac operon is induced by the addition of lactose or IPTG (isopropylthio-beta-D-galactoside). A variety of other operons, such as trp, pro, etc., are under different controls.

Specific initiation signals are also required for efficient gene transcription and translation in procaryotic cells. These transcription and translation initiation signals may vary in "strength" as measured by the quantity of gene specific messenger RNA and protein synthesized, respectively. The DNA expression vector, which contains a promotor, may also contain any combination of various "strong" transcription and/or translation initiation signals. For instance, efficient translation in *E. coli* requires an SD sequence about 7–9 bases 5' to the initiation codon ("ATG") to provide a ribosome binding site. Thus, any SD-ATG combination that can be utilized by host cell ribosomes may be employed. Such combinations include but are not limited to the SD-ATG combination from the cro gene or the N gene of coliphage lambda, or from the *E. coli* tryptophan E, D, C, B or A genes. Additionally, any SD-ATG combination produced by recombinant DNA or other techniques involving incorporation of synthetic nucleotides may be used.

Once the isolated DNA molecule encoding the human origin of recognition complex polypeptide or protein has been cloned into an expression system, it is ready to be incorporated into a host cell. Such incorporation can be carried out by the various forms of transformation noted above, depending upon the vector/host cell system. Suitable host cells include, but are not limited to, bacteria, virus, yeast, mammalian cells, insect, plant, and the like.

The invention provides efficient methods of identifying pharmacological agents or lead compounds for agents active at the level of a ORC modulatable cellular function, particularly DNA replication. Generally, these screening methods involve assaying for compounds which interfere with an ORC activity. The methods are amenable to automated, cost-effective high throughput screening of chemical libraries for lead compounds. Identified reagents find use in the pharmaceutical industries for animal and human trials; for example, the reagents may be derivatized and rescreened in in vitro and in vivo assays to optimize activity and minimize toxicity for pharmaceutical development. Target therapeutic indications are limited only in that the target cellular function be subject to modulation, usually inhibition, by disruption of the formation of a complex comprising ORC and one or more natural ORC intracellular binding targets. Target indications may include infection, cell growth and regulatory dysfunction, such as neoplasia, inflammation, hypersensitivity, etc.

A wide variety of assays for binding agents are provided including labeled in vitro kinase assays, protein-protein binding assays, immunoassays, cell based assays, etc. The ORC compositions, used to identify pharmacological agents, in isolated, partially pure or pure form and are typically recombinantly produced. The ORC may be part of a fusion product with another peptide or polypeptide (e.g., a polypeptide that is capable of providing or enhancing protein-protein binding, stability under assay conditions (e.g., a tag for detection or anchoring), etc.). The assay mixtures comprise a natural intracellular ORC binding target. While native binding targets may be used, it is frequently preferred to use portions (e.g., peptides, nucleic acid fragments) thereof so long as the portion provides binding affinity and avidity to the subject ORC conveniently measurable in the assay. The assay mixture also comprises a candidate pharmacological agent. Generally, a plurality of assay mixtures are run in parallel with different agent concentrations to obtain a differential response to the various concentrations. Typically, one of these concentrations serves as a negative control (i.e. at zero concentration or below the limits of assay detection). Candidate agents encompass numerous chemical classes, though typically they are organic compounds; preferably small organic compounds and are obtained from a wide variety of sources, including libraries of synthetic or natural compounds. A variety of other reagents may also be included in the mixture. These include reagents like salts, buffers, neutral proteins (e.g., albumin, detergents, etc.), which may be used to facilitate optimal binding and/or reduce nonspecific or background interactions, etc. Also, reagents that otherwise improve the efficiency of the assay (e.g., protease inhibitors, nuclease inhibitors, antimicrobial agents, etc.) may be used.

The invention provides ORC-specific binding agents including natural intracellular binding targets such as origin of replication (i.e. ori) sites, other ORC proteins, etc., and methods of identifying and making such agents, and their use in diagnosis, therapy, and pharmaceutical development. For example, ORC-specific agents, especially agents which modulate ORC function, are useful in a variety of diagnostic and therapeutic applications, especially where disease is associated with excessive cell growth. Novel ORC-specific binding agents include ORC-specific antibodies and other natural intracellular binding agents identified with assays such as one- and two-hybrid screens, non-natural intracellular binding agents identified in screens of chemical libraries, etc.

Generally, ORC-specificity of the binding agent is shown by binding equilibrium constants. Such agents are capable of selectively binding an ORC (i.e., with an equilibrium constant at least about $10^7$ $M^{-1}$, preferably, at least about $10^8$ $M^{-1}$, more preferably, at least about $10^9$ $M^{-1}$). A wide variety of cell-based and cell-free assays may be used to demonstrate ORC-specific binding; preferred are rapid in vitro, cell-free assays such as mediating or inhibiting ORC-protein binding, gel shift assays, immunoassays, etc.

Frequently, the assay mixtures comprise at least a portion of a nucleic acid comprising a sequence with shares sufficient sequence similarity with a gene or gene regulatory region to which the targeted ORC protein naturally binds (e.g., an ori sequence) to provide sequence-specific binding. Such a nucleic acid may further comprise one or more sequences which facilitate the binding of one or more additional ORC proteins which cooperatively bind the nucleic acid. Where used, the nucleic acid portion bound by the ORC may be continuous or segmented and is usually linear and double-stranded DNA, though circular plasmids or other nucleic acids or structural analogs may be substituted so long as ORC sequence-specific binding is retained. In some applications, supercoiled DNA provides optimal sequence-specific binding and is preferred. The nucleic acid may be of any length amenable to the assay conditions and requirements.

The resultant mixture is incubated under conditions whereby, but for the presence of the candidate pharmacological agent, the ORC specifically binds the cellular binding target, portion or analog. The mixture components can be added in any order that provides for the requisite bindings. Incubations may be performed at any temperature which facilitates optimal binding, typically between 4 and 40° C., more commonly between 15° and 40° C. Incubation periods are likewise selected for optimal binding but also minimized to facilitate rapid, high-throughput screening, and are typically between 0.1 and 10 hours, preferably less than 5 hours, more preferably less than 2 hours.

After incubation, the presence or absence of specific binding between the ORC fragment and one or more binding targets is detected by any convenient way. For cell-free binding type assays, a separation step is often used to separate bound from unbound components. Separation may be effected by precipitation (e.g., immunoprecipitation), immobilization (e.g., on a solid substrate such as a microtiter plate), etc., followed by washing.

Detection may be effected in any convenient way. For cell-free binding assays, one of the components usually comprises or is coupled to a label. A wide variety of labels may be employed—essentially any label that provides for detection of bound protein is useful. The label may provide for direct detection as radioactivity, luminescence, optical or electron density, etc. or indirect detection such as an epitope tag, an enzyme, etc. The label may be appended to the protein (e.g., a phosphate group comprising a radioactive isotope of phosphorous), or incorporated into the protein structure (e.g., a methionine residue comprising a radioactive isotope of sulfur). A variety of methods may be used to detect the label depending on the nature of the label and other assay components. For example, the label may be detected bound to the solid substrate, or a portion of the bound complex containing the label may be separated from the solid substrate, and thereafter the label detected. Labels may be directly detected through optical or electron density, radiative emissions, nonradiative energy transfer, etc. or indirectly detected with antibody conjugates, etc. For example, in the case of radioactive labels, emissions may be detected directly (e.g., with particle counters) or indirectly (e.g., with scintillation cocktails and counters).

EXAMPLES

Example 1

Isolation of ORC5

The TIGR (The Institute for Genome Research) level 2 database was searched for partial cDNA sequences and translated amino acid sequences showing sequence similarity to the *D. melanogaster* ORC5 protein sequence. One tentative human consensus sequence, THC83655, was identified. The nucleotide sequence of THC83655 had been assembled by TIGR using DNA sequence information derived from two cDNA clones, EST62176 and EST88349. These two clones were obtained and their DNA sequences determined. SEQ. ID. Nos. 3 and 4 show the cDNA and conceptual translate of EST62176. An alignment of four ORC5-related genes is shown in Table 2. The sequence alignment shows a high degree of sequence identity. For example, the human and *D. melanogaster* amino acid sequences are 35% identical. This is in line with earlier findings that ORC proteins are conserved from yeast to human.

Example 2

Sequencing ORC5

Figure 1:
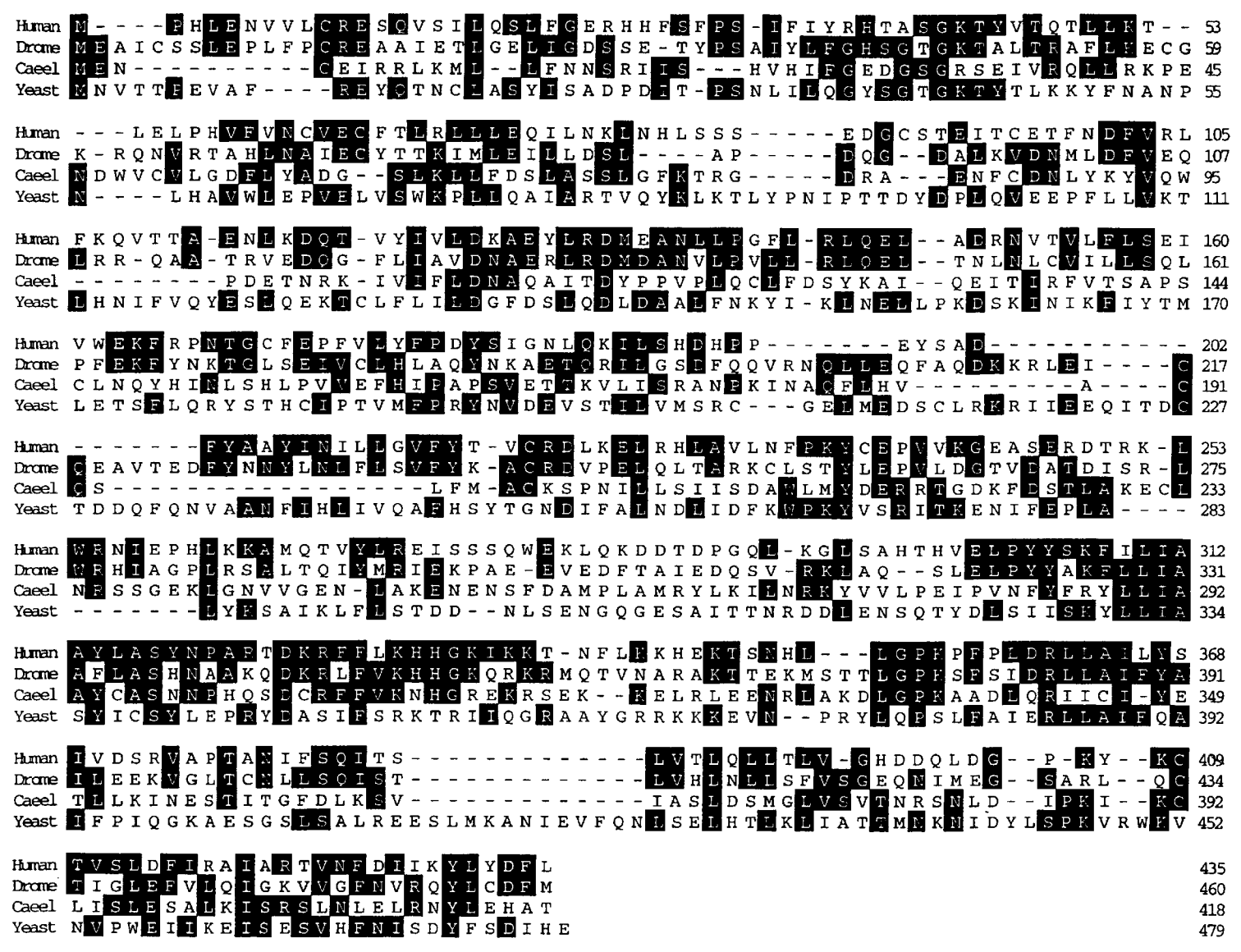

The amino acid sequence of the human ORC5 encoding gene showed significant identity and percent similarity to the corresponding genes from Drosophila (35.1%, 63.4%) and *S. cerevisiae* (19.4%, 44.4%). In addition, the human ORC5 showed 19.0% identity and 40.6% similarity to a *C. elegans* protein, zc168.3, predicted from the Nematode sequencing project at the Sanger Centre, Cambridge, UK and Department of Genetics, Washington University, St. Louis, Mo. An alignment of the four predicted amino acid sequences is shown in FIG. 1. A region that conforms to the P-loop ATP/GTP binding consensus sequence (Koonin, E. V., "A Common Set of Conserved Motifs in a Vast Variety of Putative Nucleic Acid-Dependent ATPases Including MCM Proteins Involved in the Initiation of Eukaryotic DNA Replication," *Nucleic Acid Res.*, 21:2541–47 (1993), which is hereby incorporated by reference) was found in the N-terminal region of human ORC5 (residues 37 to 44), as well as in the other four sequences (Gossen, M., et al., "A Drosophila Homolog of the Yeast Origin Recognition Complex," *Science*, 270:1674–77 (1995); Loo, S., et al., "The Origin Recognition Complex in Silencing, Cell Cycle Progression, and DNA Replication," *Mol. Biol. Cell*, 6:741–56 (1995), which are hereby incorporated by reference).

Example 3
Isolation of ORC4

A partial cDNA sequence from *M. musculus* (Genbank Accession Number AA110785), translated amino acid sequence showing sequence similarity to the *S. cerevisiae* ORC4 protein sequence was identified in the NCBI dbest database by computer-based sequence searching. A partial human cDNA sequence (Genbank Accession Number T80329) and a translated amino acid sequence showing sequence similarity to the translated amino acid sequence of the *M. musculus* cDNA sequence were then identified in the NCBI dbest database by computer-based sequence searching. The clones from which these cDNA sequences were derived were obtained from Genome Systems, Inc. and sequenced on both strands using an automated sequencer. SEQ. ID. Nos. 1 and 2 show the cDNA and conceptual translate of human ORC4. An alignment of the ORC4 genes of human and yeast is shown in FIG. 2. The human ORC4 protein contains a Walker motif (residues 67 to 74) which suggests it has an ATP/GTP nucleotide binding capability.

Example 4
Cloning ORC4

PCR (Polymerase Chain Reaction) was used to introduce unique restriction endonuclease sites at the 5' and 3' termini of ORC4. Primer 407 introduced a NdeI site and primer 408 introduced a BamHI site.

407(5' terminus NdeI site)

5' AGG GAA TTC CAT ATG AGC AGT CGT AAA TCA AAG AGT AAC AGC 3' (SEQ. ID. No. 5)

408 (3' terminus BamHI site)

5' CGC GGA TCC TCA TAA CCA GCT TAG TGA GGA TGT TGC 3' (SEQ. ID. No. 6)

The PCR amplification was performed for 30 cycles of 94° C. for 1 min, 55° C. for 1 min, and 72° C. for 1 min in a reaction volume of 0.1 ml containing 10 mM KCl, 20 mM Tris-HCl (pH 8.8 @ 25° C.), 10 mM $(NH_4)_2SO_4$, 2 mM $MgSO_4$, 0.1% Triton X-100, 200 mM each dNTP, 20 pmol each primer 407 and 408, 20 ng template (25172), 1 unit Vent$^R$(exo+). Amplified DNA products were extracted with phenol/chloroform and ethanol precipitated prior to being digested with BamHI and NdeI restriction endonucleases (digested in a BamHI buffer (NEB) with a 4 fold excess of each enzyme, for 3 hrs). Digested DNA was separated in a 1% Low Melting Agarose gel. Gel slices were melted at 70° C. for 1 hr in a 0.1 M NaCl solution. DNA was extracted with phenol twice before being precipitated with ethanol. These primers yield a 1300 nucleotide PCR product (NdeI/BamHI) which is ligated into a NdeI/BamHI digested pHK vector (5/1 ratio of insert/vector). This vector contains an upstream sequence that has a polyhistidine sequence and a recognition site for a cAMP-dependent protein kinase (*Gene*, 166: 177–178 (1995), which is hereby incorporated by reference) (FIG. 3). Ligated mix was transformed into an XL-1 Blue *E. coli* strain for insert check and plasmid amplification. The same plasmid was subsequently transformed into *E. coli* BL21 (DE3) strain for protein expression.

Example 5
ORC4 Expression and Purification from *E.coli*

A single colony was grown in 10 ml LB (Luria Broth plus 200 μg/ml Ampicillin) to a mid log phase ($OD_{595}$=0.5) and then used to innoculate a 48 L culture for protein expression. Cells were grown at 37° C. to $OD_{595}$=0.5. Following addition of 1 mM IPTG, the temperature was lowered to 15° C. for an overnight induction (16 hours). In the morning, cells were centrifuged and resuspended in $Ni^{+2}$ column buffer (5 mM imidazole, 0.5 M NaCl, 20 mM Tris, pH 7.9). Soluble supernatant was generated by passage of the cells through an Aminco French press twice (15,000 psi) followed by centrifugation for 1 hour in an SS-34 rotor at 4° C. 1 at 15,000 rpm. The cleared lysate supernatant was diluted twice with the $Ni^{+2}$ column loading buffer and loaded onto a 50 ml chelated $Ni^{+2}$ column. The column was washed with $Ni^{+2}$ column buffer containing 60 mM imidazole to remove most of the non-specifically bound proteins. ORC4 was eluted from the column with a 400 ml linear gradient of $Ni^{+2}$ column buffer containing 60 mM to 200 mM imidazole. Fractions of 2.8 ml were collected and assayed by electrophoresis on a 10% SDS-PAGE gel. Fractions containing ORC4 were pooled and precipitated with ammonium sulfate. Ammonium sulfate was added at 0.42 g/ml of protein solution (65% saturation). The solution was stirred for 15 minutes, and the precititate was allowed to settle on ice for 30 minutes. The precipitate was centrifuged for 30 minutes in a GSA rotor at 13,000 rpm. The pellet was resuspended in 1/10 volume of R buffer (25 mM Tris-HCl, pH 7.5, 20% glycerol, 5 mM DTT, 0.5 mM EDTA) containing 1 M NaCl and dialyzed twice against the same buffer. Following dialysis, the protein solution yielded 37.5 mg at a concentration of 2.5 mg/ml. The protein solution was diluted 10 times with R buffer containing 0 M NaCl prior to being loaded onto an 8 ml MonoQ (H/H 16/10) column. ORC4 was eluted from the column with an 80 ml linear gradient of R buffer containing 50 mM to 500 mM NaCl. Fractions of 1 ml were collected and assayed by electrophoresis on a 10% SDS-PAGE gel. ORC4 eluted at 200 mM NaCl. This 48 L culture yielded 20 mg of soluble ORC4 protein that was judged to be 95% pure in a Coomassie stained SDS-PAGE gel (FIG. 4). The identity of the purified protein was confirmed to be ORC4 by microsequencing of the first five amino acids.

Example 6
Expression of ORC4 in Baculovirus

PCR was used to reclone ORC4 from the original plasmid clone into the BamHI restriction endonuclease site of the baculovirus transfer vectors pBac-N-Blue 4.5 and pBac-N-Blue His 2A. Conditions for this amplification were identical to the aforementioned PCR reaction with the exception of primer sequences. Primers Iborc4P1 and IBorc4P5 introduce BamHI sites to both 5' and 3' termini of the ORC4 encoding gene. The PCR product was digested and gel purified under the aforementioned conditions. Transfer plasmids were cotransfected with linearized baculovirus DNA into the Sf9 insect cells to generate recombinant virus. Cloning and transfection conditions for baculovirus were as described in an Invitrogen Transfection kit.

IBorc4P1
5' TTT TTT CCC GGA TCC GTT AAA ATG AGC AGT CGT AAA 3' (SEQ. ID. No. 7)

IBorc4P5
5' CCC TTT AAA GGA TTC AGT CAT ATT TTA TT 3' (SEQ. ID. No. 8)

Although the invention has been described in detail for the purpose of illustration, it is understood that such detail is solely for that purpose, and variations can be made therein by those skilled in the art without departing from the spirit and scope of the invention which is defined by the following claims.

What is claimed:

1. An isolated DNA molecule encoding human origin of recognition complex subunit 4 protein or polypeptide or human origin of recognition complex subunit 5 protein or polypeptide.

2. An isolated DNA molecule according to claim 1, wherein said isolated DNA molecule encodes human origin of recognition complex subunit 4 protein or polypeptide.

3. An isolated DNA molecule according to claim 2, wherein the DNA molecule encodes a protein or polypeptide having SEQ. ID. No. 2 or is a complement thereof.

4. An isolated DNA molecule according to claim 2, wherein the DNA molecule 1) has a nucleotide sequence of SEQ. ID. No. 1 or 2) has a nucleotide sequence which hybridizes to SEQ. ID. No. 1 under stringent conditions or 3) is a complement of 1) or 2).

5. An isolated DNA molecule according to claim 1, wherein said isolated DNA molecule encodes human origin of recognition complex subunit 5 protein or polypeptide.

6. An isolated DNA molecule according to claim 5, wherein the DNA molecule encodes a protein or polypeptide having SEQ. ID. No. 4 or is a complement thereof.

7. An isolated DNA molecule according to claim 5, wherein the DNA molecule 1) has a nucleotide sequence of SEQ. ID. No. 3 or 2) has a nucleotide sequence which hybridizes to SEQ. ID. No. 3 under stringent conditions or 3) is a complement of 1 or 2).

8. An expression system containing a heterologous DNA molecule according to claim 1.

9. An expression system according to claim 8, wherein the DNA molecule is in correct reading frame and sense orientation.

10. An expression system according to claim 8, wherein said DNA molecule encodes human origin of recognition complex subunit 4 protein or polypeptide.

11. An expression system according to claim 10, wherein the DNA molecule encodes a protein or polypeptide having SEQ. ID. No. 2 or is a complement thereof.

12. An expression system according to claim 10, wherein the DNA molecule 1) has a nucleotide sequence of SEQ. ID. No. 1 or 2) has a nucleotide sequence which hybridizes to SEQ. ID. No. 1 under stringent conditions or 3) is a complement of 1) or 2).

13. An expression system according to claim 8, wherein the DNA molecule encodes human origin of recognition complex subunit 5 protein or polypeptide.

14. An expression system according to claim 13, wherein the DNA molecule encodes a protein or polypeptide having SEQ. ID. No. 4 or is a complement thereof.

15. An expression system according to claim 13, wherein the DNA molecule 1) has a nucleotide sequence of SEQ. ID. No. 3 or 2) has a nucleotide sequence which hybridizes to SEQ. ID. No. 3 under stringent conditions or 3) is a complement of 1) or 2).

16. A host cell transformed with a heterologous DNA molecule according to claim 1.

17. A host cell according to claim 16, wherein the DNA molecule is in an expression vector.

18. A host cell according to claim 16, wherein said DNA molecule encodes human origin of recognition complex subunit 4 protein or polypeptide.

19. A host cell according to claim 18, wherein the DNA molecule encodes a protein or polypeptide having SEQ. ID. No. 2 or is a complement thereof.

20. A host cell according to claim 18, wherein the DNA molecule 1) has a nucleotide sequence of SEQ. ID. No. 1 or 2) has a nucleotide sequence which hybridizes to SEQ. ID. No. 1 under stringent conditions or 3) is a complement of 1) or 2).

21. A host cell according to claim 16, wherein the DNA molecule encodes human origin of recognition complex subunit 5 protein or polypeptide.

22. A host cell according to claim 21, wherein the DNA molecule encodes a protein or polypeptide having SEQ. ID. No. 4 or is a complement thereof.

23. A host cell according to claim 21, wherein the DNA molecule 1) has a nucleotide sequence of SEQ. ID. No. 3 or 2) has a nucleotide sequence which hybridizes to SEQ. ID. No. 3 under stringent conditions or 3) is a complement of 1) or 2).

* * * * *

SEQUENCE LISTING

<160> NUMBER OF SEQ ID NOS: 8

<210> SEQ ID NO 1
<211> LENGTH: 1308
<212> TYPE: DNA
<213> ORGANISM: Homo sapiens

<400> SEQUENCE: 1

```
atgccccact tggaaaacgt ggtgctttgt cgcgagtctc aagtgtccat cttgcagtcc      60
ttgtttggag agagacatca tttcagcttt ccatccattt ttatttatag acatactgct     120
agtggaaaga cctatgtaac acaaacgttg ttgaaaactt tagagctccc acatgtgttt     180
gtgaattgtg ttgaatgctt tacattgagg ctgcttttgg aacaaatttt aaacaaattg     240
aatcatctta gttcttcaga ggatggatgt tctactgaaa taacctgtga acatttaat      300
gactttgttc gcttgtttaa acaagtaacc acagctgaaa atcttaaaga tcagactgta     360
tatattgttc tagataaagc agagtatcta agagatatgg aagcaaatct tttgcctgga     420
tttcttagat tacaagaatt ggctgacaga aatgtgactg ttctctttct cagtgaaatt     480
gtttgggaaa agtttcgtcc aaatactgga tgctttgagc cgtttgtctt atatttccct     540
gattacagca taggcaacct tcaaaagatc ctgtcccatg atcatcctcc agagtattca     600
gctgatttct atgctgccta cattaacatt cttcttggag ttttctacac tgtttgtcga     660
gatttgaaag agctcagaca tctggcagta cttaattttc ctaaatattg tgaacccgtg     720
gttaaaggag aagcaagtga acgtgatact cgcaaactgt ggagaaatat tgaacctcat     780
ttgaagaaag ctatgcagac tgtttatctc agggaaatat caagttccca gtgggaaaag     840
ctacagaaag atgcacagag tccggggcaa ctgaaaggcc tctcagcgca tactcatgtg     900
gaacttccat attactctaa gttcattcta attgctgcat accttgcttc atacaatcca     960
gcaagaactg acaagaggtt ttttcttaag catcatggaa aaatcaagaa aaccaacttt    1020
ctaaaaaaac acgaaaagac aagcaatcat ctccttgggc caaaccatt tccactagac     1080
agattattag caatattata tagtatcgtg gacagcagag ttgctccaac agcaaatatt    1140
ttttcccaga ttacctctct agtgacccTt cagctgttaa ccctggttgg ccatgacgat    1200
cagcttgatg gaccaaaata caaatgcaca gtgtctctag acttcatcag agctattgca    1260
aggacggtga actttgacat aataaaatac ttgtatgatt tcttgtga                 1308
```

<210> SEQ ID NO 2
<211> LENGTH: 435
<212> TYPE: PRT
<213> ORGANISM: Homo sapiens

<400> SEQUENCE: 2

```
Met Pro His Leu Glu Asn Val Val Leu Cys Arg Glu Ser Gln Val Ser
  1               5                  10                  15

Ile Leu Gln Ser Leu Phe Gly Glu Arg His His Phe Ser Phe Pro Ser
             20                  25                  30
```

```
Ile Phe Ile Tyr Arg His Thr Ala Ser Gly Lys Thr Tyr Val Thr Gln
         35                  40                  45

Thr Leu Leu Lys Thr Leu Glu Leu Pro His Val Phe Val Asn Cys Val
     50                  55                  60

Glu Cys Phe Thr Leu Arg Leu Leu Glu Gln Ile Leu Asn Lys Leu
 65              70                  75                  80

Asn His Leu Ser Ser Ser Glu Asp Gly Cys Ser Thr Glu Ile Thr Cys
                 85                  90                  95

Glu Thr Phe Asn Asp Phe Val Arg Leu Phe Lys Gln Val Thr Thr Ala
                100                 105                 110

Glu Asn Leu Lys Asp Gln Thr Val Tyr Ile Val Leu Asp Lys Ala Glu
            115                 120                 125

Tyr Leu Arg Asp Met Glu Ala Asn Leu Leu Pro Gly Phe Leu Arg Leu
        130                 135                 140

Gln Glu Leu Ala Asp Arg Asn Val Thr Val Leu Phe Leu Ser Glu Ile
145                 150                 155                 160

Val Trp Glu Lys Phe Arg Pro Asn Thr Gly Cys Phe Glu Pro Phe Val
                165                 170                 175

Leu Tyr Phe Pro Asp Tyr Ser Ile Gly Asn Leu Gln Lys Ile Leu Ser
                180                 185                 190

His Asp His Pro Pro Glu Tyr Ser Ala Asp Phe Tyr Ala Ala Tyr Ile
        195                 200                 205

Asn Ile Leu Leu Gly Val Phe Tyr Thr Val Cys Arg Asp Leu Lys Glu
        210                 215                 220

Leu Arg His Leu Ala Val Leu Asn Phe Pro Lys Tyr Cys Glu Pro Val
225                 230                 235                 240

Val Lys Gly Glu Ala Ser Glu Arg Asp Thr Arg Lys Leu Trp Arg Asn
                245                 250                 255

Ile Glu Pro His Leu Lys Lys Ala Met Gln Thr Val Tyr Leu Arg Glu
            260                 265                 270

Ile Ser Ser Ser Gln Trp Glu Lys Leu Gln Lys Asp Asp Thr Asp Pro
        275                 280                 285

Gly Gln Leu Lys Gly Leu Ser Ala His Thr His Val Glu Leu Pro Tyr
290                 295                 300

Tyr Ser Lys Phe Ile Leu Ile Ala Ala Tyr Leu Ala Ser Tyr Asn Pro
305                 310                 315                 320

Ala Arg Thr Asp Lys Arg Phe Phe Leu Lys His His Gly Lys Ile Lys
                325                 330                 335

Lys Thr Asn Phe Leu Lys Lys His Glu Lys Thr Ser Asn His Leu Leu
            340                 345                 350

Gly Pro Lys Pro Phe Pro Leu Asp Arg Leu Leu Ala Ile Leu Tyr Ser
        355                 360                 365

Ile Val Asp Ser Arg Val Ala Pro Thr Ala Asn Ile Phe Ser Gln Ile
    370                 375                 380

Thr Ser Leu Val Thr Leu Gln Leu Leu Thr Leu Val Gly His Asp Asp
385                 390                 395                 400

Gln Leu Asp Gly Pro Lys Tyr Lys Cys Thr Val Ser Leu Asp Phe Ile
                405                 410                 415

Arg Ala Ile Ala Arg Thr Val Asn Phe Asp Ile Ile Lys Tyr Leu Tyr
            420                 425                 430

Asp Phe Leu
        435
```

<210> SEQ ID NO 3
<211> LENGTH: 1311
<212> TYPE: DNA
<213> ORGANISM: Homo sapiens

<400> SEQUENCE: 3

```
atgagcagtc gtaaatcaaa gagtaacagc ttaattcaca cagagtgcct ttcacaggta      60
caaagaattt tacgtgaaag attttgtcgt cagagtccac atagtaacct atttggagtg     120
caagtacaat acaaacactt aagtgagctg ctgaaaagaa ctgctctcca tggagagagt     180
aactctgtcc ttattatcgg accccgagga tcaggaaaaa ctatgttaat aagtcatgct     240
ttgaaagaac tcatggaaat agaagaagtg agtgaaaatg tattacaagt tcacttaaat     300
ggactgctgc agatcaatga caaatcgcc ctaaggaaa tcacaaggca gttaaatctg      360
gaaaatgtag ttggagataa agtttttgga agctttgctg aaaacctttc atttcttctg     420
gaagctttaa aaaaggtga ccgaactagc agttgcccag tgatcttcat attagatgaa      480
tttgatcttt ttgctcatca taaaaaccaa acacttctct ataatctttt tgacatttct     540
cagtctgcac agaccccaat agcagttatt ggtcttacat gtagattgga tattttggaa     600
ctcttagaaa aaagagtgaa gtcaagattt tctcaccggc agatacactt aatgaattca     660
tttggttttc cacagtatgt taaaatattt aagaacagt tatctctacc tgcagagttt       720
ccagacaagg ttttttgctga gaagtggaat gaaaatgttc agtatctctc agaagataga     780
agtgtgcaag aagtactaca gaagcatttc aatatcagca aaaacctgcg gtcattacac     840
atgctattga tgcttgcttt aaatcgagta acagcatcgc acccatttat gactgccgta     900
gatctaatgg aagcaagcca actgtgtagc atggactcga agcaaatat tgtacatggt       960
ctatcagtct tggaaatctg tcttataata gcaatgaaac atttaaatga catctatgag    1020
gaagagccat ttaattttca aatggtctat aatgagtttc agaagtttgt tcaaaggaaa    1080
gcacattccg tttataattt tgaaaaacct gttgtcatga aggcttttga acacttgcag    1140
caattagaat taataaagcc catggaaaga acttcaggaa attcacagag agagtaccag    1200
ctgatgaaac tgcttttgga taatactcaa attatgaatg ctctgcagaa atatcccaac    1260
tgtcctacag atgtgaggca gtgggcaaca tcctcactaa gctggttatg a             1311
```

<210> SEQ ID NO 4
<211> LENGTH: 436
<212> TYPE: PRT
<213> ORGANISM: Homo sapiens

<400> SEQUENCE: 4

```
Met Ser Ser Arg Lys Ser Lys Ser Asn Ser Leu Ile His Thr Glu Cys
  1               5                  10                  15

Leu Ser Gln Val Gln Arg Ile Leu Arg Glu Arg Phe Cys Arg Gln Ser
             20                  25                  30

Pro His Ser Asn Leu Phe Gly Val Gln Val Gln Tyr Lys His Leu Ser
         35                  40                  45

Glu Leu Leu Lys Arg Thr Ala Leu His Gly Glu Ser Asn Ser Val Leu
     50                  55                  60

Ile Ile Gly Pro Arg Gly Ser Gly Lys Thr Met Leu Ile Ser His Ala
 65                  70                  75                  80

Leu Lys Glu Leu Met Glu Ile Glu Glu Val Ser Glu Asn Val Leu Gln
                 85                  90                  95

Val His Leu Asn Gly Leu Leu Gln Ile Asn Asp Lys Ile Ala Leu Lys
            100                 105                 110
```

Glu Ile Thr Arg Gln Leu Asn Leu Glu Asn Val Val Gly Asp Lys Val
         115                 120                 125

Phe Gly Ser Phe Ala Glu Asn Leu Ser Phe Leu Leu Glu Ala Leu Lys
         130                 135                 140

Lys Gly Asp Arg Thr Ser Ser Cys Pro Val Ile Phe Ile Leu Asp Glu
145                 150                 155                 160

Phe Asp Leu Phe Ala His His Lys Asn Gln Thr Leu Leu Tyr Asn Leu
                 165                 170                 175

Phe Asp Ile Ser Gln Ser Ala Gln Thr Pro Ile Ala Val Ile Gly Leu
                 180                 185                 190

Thr Cys Arg Leu Asp Ile Leu Glu Leu Leu Glu Lys Arg Val Lys Ser
         195                 200                 205

Arg Phe Ser His Arg Gln Ile His Leu Met Asn Ser Phe Gly Phe Pro
         210                 215                 220

Gln Tyr Val Lys Ile Phe Lys Glu Gln Leu Ser Leu Pro Ala Glu Phe
225                 230                 235                 240

Pro Asp Lys Val Phe Ala Glu Lys Trp Asn Glu Asn Val Gln Tyr Leu
                 245                 250                 255

Ser Glu Asp Arg Ser Val Gln Glu Val Leu Gln Lys His Phe Asn Ile
                 260                 265                 270

Ser Lys Asn Leu Arg Ser Leu His Met Leu Leu Met Leu Ala Leu Asn
         275                 280                 285

Arg Val Thr Ala Ser His Pro Phe Met Thr Ala Val Asp Leu Met Glu
         290                 295                 300

Ala Ser Gln Leu Cys Ser Met Asp Ser Lys Ala Asn Ile Val His Gly
305                 310                 315                 320

Leu Ser Val Leu Glu Ile Cys Leu Ile Ile Ala Met Lys His Leu Asn
                 325                 330                 335

Asp Ile Tyr Glu Glu Pro Phe Asn Phe Gln Met Val Tyr Asn Glu
                 340                 345                 350

Phe Gln Lys Phe Val Gln Arg Lys Ala His Ser Val Tyr Asn Phe Glu
         355                 360                 365

Lys Pro Val Val Met Lys Ala Phe Glu His Leu Gln Gln Leu Glu Leu
370                 375                 380

Ile Lys Pro Met Glu Arg Thr Ser Gly Asn Ser Gln Arg Glu Tyr Gln
385                 390                 395                 400

Leu Met Lys Leu Leu Leu Asp Asn Thr Gln Ile Met Asn Ala Leu Gln
                 405                 410                 415

Lys Tyr Pro Asn Cys Pro Thr Asp Val Arg Gln Trp Ala Thr Ser Ser
                 420                 425                 430

Leu Ser Trp Leu
         435

<210> SEQ ID NO 5
<211> LENGTH: 42
<212> TYPE: DNA
<213> ORGANISM: Artificial Sequence
<220> FEATURE:
<223> OTHER INFORMATION: Description of Artificial Sequence:  PCR primer

<400> SEQUENCE: 5
agggaattcc atatgagcag tcgtaaatca aagagtaaca gc                          42

<210> SEQ ID NO 6
<211> LENGTH: 36

```
<212> TYPE: DNA
<213> ORGANISM: Artificial Sequence
<220> FEATURE:
<223> OTHER INFORMATION: Description of Artificial Sequence:  PCR primer

<400> SEQUENCE: 6
cgcggatcct cataaccagc ttagtgagga tgttgc                                      36

<210> SEQ ID NO 7
<211> LENGTH: 36
<212> TYPE: DNA
<213> ORGANISM: Artificial Sequence
<220> FEATURE:
<223> OTHER INFORMATION: Description of Artificial Sequence:  PCR primer

<400> SEQUENCE: 7
tttttccccg gatccgttaa aatgagcagt cgtaaa                                      36

<210> SEQ ID NO 8
<211> LENGTH: 29
<212> TYPE: DNA
<213> ORGANISM: Artificial Sequence
<220> FEATURE:
<223> OTHER INFORMATION: Description of Artificial Sequence:  PCR primer

<400> SEQUENCE: 8
ccctttaaag gattcagtca tattttatt                                              29
```